(12) United States Patent
Patel et al.

(10) Patent No.: US 9,636,331 B2
(45) Date of Patent: May 2, 2017

(54) COMPOSITIONS AND METHODS FOR TREATING BACTERIAL INFECTIONS

(71) Applicant: WOCKHARDT LIMITED, Aurangabad (IN)

(72) Inventors: Mahesh Vithalbhai Patel, Aurangabad (IN); Sachin Bhagwat, Aurangabad (IN); Prasad Keshav Deshpande, Aurangabad (IN)

(73) Assignee: WOCKHARDT LIMITED, Chikalthana (IN)

( * ) Notice: Subject to any disclaimer, the term of this patent is extended or adjusted under 35 U.S.C. 154(b) by 0 days.

(21) Appl. No.: 15/076,004

(22) Filed: Mar. 21, 2016

(65) Prior Publication Data

US 2016/0199360 A1  Jul. 14, 2016

Related U.S. Application Data

(62) Division of application No. 14/442,135, filed as application No. PCT/IB2014/058221 on Jan. 13, 2014, now Pat. No. 9,433,613.

(30) Foreign Application Priority Data

Jan. 14, 2013 (IN) .......................... 117/MUM/2013

(51) Int. Cl.
  *A61K 31/427*  (2006.01)
  *A61K 31/439*  (2006.01)
  *A61K 31/546*  (2006.01)
  *A61K 45/06*   (2006.01)
  *A61K 31/431*  (2006.01)
  *A61K 31/407*  (2006.01)

(52) U.S. Cl.
  CPC .......... *A61K 31/439* (2013.01); *A61K 31/407* (2013.01); *A61K 31/427* (2013.01); *A61K 31/431* (2013.01); *A61K 31/546* (2013.01); *A61K 45/06* (2013.01)

(58) Field of Classification Search
  CPC .. A61K 31/427; A61K 31/439; A61K 31/546; A61K 45/06
  See application file for complete search history.

(56) References Cited

FOREIGN PATENT DOCUMENTS

| WO | WO2007/129176 A2 | 11/2007 |
|----|------------------|---------|
| WO | WO2013/030733 A1 | 3/2013  |

OTHER PUBLICATIONS

Overcoming enzymatic resistance in bacteria: impact on future therapy. Labia et al., J Int Med Res. 1990;18 Suppl 4:48D-57D.
A review of the antimicrobial activity of clavulanate. Finlay et al. J. Antimicrob. Chemother. (2003) 52 (1): 18-23.

*Primary Examiner* — Sahar Javanmard
(74) *Attorney, Agent, or Firm* — Bio Intellectual Property Services LLC; O. (Sam) Zaghmout

(57) ABSTRACT

Pharmaceutical compositions and methods for treating bacterial infections are disclosed.

11 Claims, No Drawings

COMPOSITIONS AND METHODS FOR TREATING BACTERIAL INFECTIONS

CROSS-REFERENCE TO RELATED APPLICATIONS

This application is a division of U.S. application Ser. No. 14/442,135, filed May 12, 2015, now pending, which entered the National Phase of Serial No. PCT/IB2014/058221, filed Jan. 13, 2014, which claims priority to Indian patent application 117/MUM/2013, filed Jan. 14, 2013. The entire disclosure of these prior applications are hereby incorporated by reference.

FIELD OF THE INVENTION

The invention relates to compositions and methods for treating bacterial infections.

BACKGROUND OF THE INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistance. Coates et al. (Br. J. Pharmacol. 2007; 152(8), 1147-1154) have reviewed novel approaches to developing new antibiotics. However, the development of new antibacterial agents is a challenging task. For example, Gwynn et al. (Annals of the New York Academy of Sciences, 2010, 1213: 5-19) have reviewed the challenges in the discovery of antibacterial agents.

In general, majority of the antibacterial agents in use today belong to the beta-lactam class of antibacterial agents (such as, for example, penicillins, cephalosporins, carbapenems, monobactams etc.) owing to their established efficacy and safety. In addition, the beta-lactam class of antibacterial agents has consistently remained attractive due to their chemical maneuverability thereby generating clinically relevant agents with a diverse therapeutic profile. The beta-lactam class of antibacterial agents target several bacterial enzymes, collectively termed as penicillin binding proteins (PBPs) located on cytoplasmic membrane facing periplasmic space. PBPs are necessary for growth and maintenance of peptidoglycan layer, which forms part of the bacterial cell wall and protects the cell from osmotic stress. Inhibition of peptidoglycan biosynthesis therefore results in bacterial cell growth inhibition and/or killing. The ability of various beta-lactam compounds to act as antibacterial agents originates from their ability to bind with one or more PBPs and interfere with the bacterial cell wall synthesis. Thus, inhibition of essential high molecular weight PBPs such as PBPs 1a or 1b, 2 and 3 is critical for bacterial cell lysis. Agents that bind to more than one essential PBP with high affinities are significantly more cidal as compared to agents that bind to single PBPs.

Heavy use of antibacterial agents has resulted in bacteria developing resistance to known antibacterial agents through various mechanisms. For example, resistance in *Staphylococci* is mediated by synthesis of penicillinase and acquisition of modified PBP2a by the bacteria. Modifications in the target PBPs has also played an important role in the development of resistance to beta-lactam antibacterial agents. A more common mechanism by which bacteria acquire resistance to beta-lactam antibacterial agents is by producing beta-lactamase enzymes, which inactivate the beta-lactam antibacterial agents. To some extent, this problem was overcome by using various beta-lactamase inhibitors (for example, clavulanic acid, sulbactam etc.). However, this approach too has limitations. For example, clinically available effective inhibitors for carbapenem hydrolyzing oxacillinases and metallo beta-lactamase enzymes are not available. This means, treatment options for infections caused by pathogens expressing such extended spectrum beta-lactamases (ESBL) are limited to the agents such as colistin which is associated with severe adverse effects and inconsistent efficacy.

In view of this, there is an urgent need to resurrect otherwise well-established but now compromised beta-lactam antibacterial agents in a manner that could bypass the need for inhibiting diverse beta-lactamase enzymes and provide an effective approach for treating infections caused by strains expressing multiple mechanisms of beta-lactam resistance including suboptimal drug uptake. The inventors have now surprisingly discovered pharmaceutical compositions and methods for treating bacterial infections, including those caused by resistant bacteria. The composition and methods according to the invention use at least one antibacterial agent or a pharmaceutically acceptable derivative thereof, in combination with an enhancer compound or a pharmaceutically acceptable derivative thereof; wherein the enhancer compound is: (i) beta-lactamase stable, and (ii) a selective and high affinity PBP binder.

SUMMARY OF THE INVENTION

Accordingly, there are provided compositions and methods for treating bacterial infections.

In one general aspect, there is provided a pharmaceutical composition comprising: (a) at least one antibacterial agent or a pharmaceutically acceptable derivative thereof, and (b) an enhancer compound or a pharmaceutically acceptable derivative thereof; wherein the enhancer compound is: (i) beta-lactamase stable, and (ii) a selective and high affinity PBP binder.

In another general aspect, there is provided a method of treating a bacterial infection in a subject comprising the step of administering to the subject: (a) at least one antibacterial agent or a pharmaceutically acceptable derivative thereof, and (b) an enhancer compound or a pharmaceutically acceptable derivative thereof; wherein the enhancer compound is: (i) beta-lactamase stable, and (ii) a selective and high affinity PBP binder.

In another general aspect, there is provided a method for increasing antibacterial effectiveness of an antibacterial agent in a subject, said method comprising co-administering said antibacterial agent or a pharmaceutically acceptable derivative thereof, with an enhancer compound or a pharmaceutically acceptable derivative thereof; wherein the enhancer compound is: (i) beta-lactamase stable, and (ii) a selective and high affinity PBP binder.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended.

Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety as if fully rewritten herein.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "pharmaceutically acceptable derivative" as used herein refers to and includes any pharmaceutically acceptable salts, pro-drugs, metabolites, esters, ethers, hydrates, polymorphs, solvates, complexes, enantiomers or adducts of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salt, pro-drugs, metabolites, esters, ethers, hydrates, polymorphs, solvates, complexes, enantiomers or adducts) which, upon administration to a subject, is capable of providing (directly or indirectly) the antibacterial compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (J. Pharmaceutical Sciences, 66: 1-19 (1977)), incorporated herein by reference in its entirety, describes various pharmaceutically acceptable salts in details.

The term "enhancer compound" as used herein refers to compounds capable of enhancing antibacterial activity of the antibacterial agent. The term "enhancing" also indicates increasing the antibacterial activity of the antibacterial agent in sensitive as well as resistant organisms.

The term "PBP" as used herein refers to "Penicillin-binding protein", which are a group of proteins having a key role in bacterial cell wall synthesis.

The term "PBP binder" as used herein refers to a compound capable of binding to one or more PBPs, reversibly or irreversibly. The term "PBP binder" also includes compounds capable of inhibiting the activity one or more PBPs, either partially or completely.

The phrase "selective and high affinity PBP binder" refers to a PBP binder which binds to only one PBP with very high affinity. In general, the term "selective and high affinity PBP binder" also includes those binders where a substantial fraction of binder selectively binds to only one PBP with high affinity. For example, a compound may be said to be a "selective and high affinity PBP binder" if it exhibits an $IC_{50}$ value of 1 µg/ml or less to only one of the PBPs present in the organism. The term "$IC_{50}$ value" of a compound refers to the concentration of the compound that reduces the binding of Bocillin-FL to PBPs by 50% as compared to when no compound was added to the reaction.

The term "Extended spectrum beta-lactamse or ESBL" as used herein includes those beta-lactamase enzymes which are capable of conferring bacterial resistance to the penicillins, first-, second-, and third-generation cephalosporins, and aztreonam by hydrolysis of these antibiotics.

The term "MIC" as used herein refers to minimum inhibitory concentration, which is the minimum concentration of an antibacterial agent that will inhibit the visible growth of microorganisms.

The term "MSC" as used herein refers to minimum spheroplasting concentration, which is the minimum concentration of an antibacterial agent at which about 80% of bacterial cells covert into spheroplasts.

The term "MFC" as used herein refers to minimum filamentation concentration, which is the minimum concentration of an antibacterial agent at which about 80% of bacterial cells get elongated to form filament like structures.

The term "spheroplast" as used herein refers to bacterial cell from which the cell wall has been almost completely removed, by the action of an antibacterial agent.

The term "filament" as used herein refers to elongated bacterial cell.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance capable of hydrolyzing a beta-lactam ring, either partially or completely. The term "beta-lactamase" includes enzymes that are produced by bacteria and have the ability to hydrolyze or inactivate the beta-lactam ring in a beta-lactam compound, either partially or completely.

The term "beta-lactamase stable PBP binder" refers to a PBP binder that is not inactivated or hydrolyzed in presence of one or more beta-lactamase enzymes.

The term "infection" or "bacterial infection" as used herein refers to presence of bacteria, in or on a subject, which, if its growth were inhibited, would result in a benefit to the subject. As such, the term "infection" in addition to referring to the presence of bacteria also refers to normal flora, which is not desirable. The term "infection" or "bacterial infection" also includes infections caused by gram-positive and gram-negative bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition comprising more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "pharmaceutically inert ingredient" or "carrier" or "excipient" refers to a compound or material used to facilitate administration of a compound, including for example, to increase the solubility of the compound. Typical, non-limiting examples of solid carriers include, starch, lactose, dicalcium phosphate, sucrose, and kaolin and so on. Typical, non-limiting examples of liquid carriers include sterile water, saline, buffers, non-ionic surfactants, and edible oils such as oil, peanut and sesame oils and so on. In addition, various adjuvants commonly used in the art may be included. These and other such compounds are described in the literature, for example, in the Merck Index (Merck & Company, Rahway, N.J.). Considerations for inclusion of various components in pharmaceutical compositions are described, for example, in Gilman et al. (Eds.) (1990); Goodman and Gilman's: The Pharmacological Basis of Therapeutics, 8th Ed., Pergamon Press, which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

In one general aspect, there is provided a pharmaceutical composition comprising: (a) at least one antibacterial agent or a pharmaceutically acceptable derivative thereof, and (b) an enhancer compound or a pharmaceutically acceptable derivative thereof; wherein the enhancer compound is: (i) beta-lactamase stable, and (ii) a selective and high affinity PBP binder.

In another general aspect, there is provided a method of treating a bacterial infection in a subject comprising the step of administering to the subject an effective amount of a pharmaceutical composition comprising: (a) at least one antibacterial agent or a pharmaceutically acceptable derivative thereof, and (b) an enhancer compound or a pharmaceutically acceptable derivative thereof; wherein the enhancer compound is: (i) beta-lactamase stable, and (ii) a selective and high affinity PBP binder.

In yet another general aspect, there is provided a method of treating a bacterial infection in a subject comprising the step of administering to the subject (a) at least one antibacterial agent or a pharmaceutically acceptable derivative thereof, and (b) an enhancer compound or a pharmaceutically acceptable derivative thereof; wherein the enhancer compound is: (i) beta-lactamase stable, and (ii) a selective and high affinity PBP binder.

In another general aspect, there is provided a method for increasing antibacterial effectiveness of an antibacterial agent in a subject, said method comprising co-administering said antibacterial agent or a pharmaceutically acceptable derivative thereof, with an enhancer compound or a pharmaceutically acceptable derivative thereof; wherein the enhancer compound is: (i) beta-lactamase stable, and (ii) a selective and high affinity PBP binder.

The compositions and method according to the invention use an antibacterial agent or a pharmaceutically acceptable derivative thereof. A wide variety of antibacterial agents can be used. Typical, non-limiting examples of antibacterial agents include one or more of antibacterial compounds generally classified as aminoglycosides, ansamycins, carbacephems, penems, oxapenams, sulphonepenams carbapenems, cephalosporins, cephamycins, lincosamides, lipopeptides, macrolides, monobactams, nitrofurans, penicillins, polypeptides, quinolones, sulfonamides, tetracyclines, oxazolidinone and the like.

In some embodiments, in the compositions and methods according to the invention, the antibacterial agent is a beta-lactam antibacterial agent. In some other embodiments, in the compositions and methods according to the invention, the antibacterial agent is selected from a group consisting of aminoglycosides, ansamycins, carbacephems, penems, carbapenems, cephalosporins, cephamycins, lincosamides, lipopeptides, macrolides, monobactams, nitrofurans, penicillins, polypeptides, quinolones, sulfonamides, tetracyclines, or oxazolidinone antibacterial agents.

Typical, non-limiting examples of aminoglycoside antibacterial agents include Amikacin, Gentamicin, Kanamycin, Neomycin, Netilmicin, Tobramycin, Paromomycin, Arbekacin, Plazomicin, Streptomycin, Apramycin and the like.

Typical, non-limiting examples of ansamycin antibacterial agents include Geldanamycin, Herbimycin and the like.

Typical, non-limiting examples of carbacephem antibacterial agents include Loracarbef and the like.

Typical, non-limiting examples of penem antibacterial agents include Faropenem and the like.

Typical, non-limiting examples of carbapenem antibacterial agents include Ertapenem, Doripenem, Imipenem, Meropenem and the like.

Typical, non-limiting examples of cephalosporin and cephamycin antibacterial agents include Cefazolin, Cefacetrile, Cefadroxil, Cephalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cephamycin, Cefoxitin, Cefotetan, Cefmetazole, Carbacephem, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Oxacephem, Cefepime, Cefozopran, Cefpirome, Cefquinome, Ceftiofur, Cefquinome, Cefovecin, CXA-101, Ceftaroline, Ceftobiprole etc.

Typical, non-limiting examples of lincosamide antibacterial agents include Clindamycin, Lincomycin and the like.

Typical, non-limiting examples of macrolide antibacterial agents include Azithromycin, Clarithromycin, Dirithromycin, Erythromycin, Roxithromycin, Troleandomycin, Telithromycin, Spectinomycin, Solithromycin and the like.

Typical, non-limiting examples of monobactam antibacterial agents include Aztreonam and the like.

Typical, non-limiting examples of nitrofuran antibacterial agents include Furazolidone, Nitrofurantoin and the like.

Typical, non-limiting examples of penicillin antibacterial agents include Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin and the like.

Typical, non-limiting examples of polypeptide antibacterial agents include Bacitracin, Colistin, Polymyxin B and the like.

Typical, non-limiting examples of quinolone antibacterial agents include Ciprofloxacin, Enoxacin, Gatifloxacin, Levofloxacin, Lomefloxacin, Moxifloxacin, Nalidixic acid, Levonadifloxacin, Norfloxacin, Ofloxacin, Trovafloxacin, Grepafloxacin, Sparfloxacin, Temafloxacin, Delafloxacin and the like.

Typical, non-limiting examples of sulfonamide antibacterial agents include Mafenide, Sulfonamidochrysoidine, Sulfacetamide, Sulfadiazine, Sulfamethizole, Sulfamethoxazole, Sulfasalazine, Sulfisoxazole, Trimethoprim and the like.

Typical, non-limiting examples of tetracycline antibacterial agents include Demeclocycline, Doxycycline, Minocycline, Oxytetracycline, Tetracycline, Tigecycline and the like.

Typical, non-limiting examples of oxazolidinone antibacterial agents include Tedizolid, Linezolid, Ranbezolid, Torezolid, Radezolid etc The compositions and methods according to the invention use an enhancer compound or a pharmaceutically acceptable derivative thereof. The enhancer compound is (i) beta-lactamase stable, and (ii) a selective and high affinity PBP binder. In general, any selective and high affinity PBP binder which is beta-lactamase stable can be used. In general, a compound (e.g. a PBP binder) is beta-lactamase stable if it is not inactivated or hydrolyzed in presence of one or more beta-lactamase enzymes. For example, a compound (or a PBP binder) is said to be beta-lactamase stable if it retains original activity for more than two hours in presence of one or more beta-lactamase enzymes.

Typical, non-limiting examples of suitable enhancer compounds according to the invention are disclosed in PCT International Application No. PCT/IB2012/054290, PCT/IB2012/054296 and in Indian Provisional Patent Application No. 2471/MUM/2012. Variety of other compounds that are capable of acting as beta-lactamase stable, selective and high PBP binder can be used as an enhancer compound according to the invention.

In some embodiments, the enhancer compound or a pharmaceutically acceptable derivative thereof is present an amount from about 0.01 to 10 gm per gram of the antibacterial agent or a pharmaceutically acceptable derivative thereof.

In some other embodiments, the enhancer compound is capable of selectively binding to one of the essential PBPs. It is generally accepted that PBPs 1a & 1b intervene in cell wall elongation, PBP2 is required for maintenance of cell shape in its cocco bacillary form, and PBP3 participates in the formation of septum facilitating cell division. As a result, a PBP3 targeting agents brings about the conversion of cocco bacillary shape to elongated filaments. Similarly, PBP2 binding agent converts the organisms in to round shaped cells known as spheroplasts.

In some embodiments, the enhancer compound and the antibacterial agent exhibit complementary PBP binding profiles, which means that the enhancer compound is capable of selectively binding to a PBP with high affinity and the antibacterial agent is capable of binding to at least one PBP other than the one bound by the enhancer compound.

In some embodiments, there is provided a pharmaceutical composition comprising: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, and the enhancer compound or a pharmaceutically acceptable derivative thereof, are complementary PBP binding agents.

In some embodiments, there is provided a method of treating a bacterial infection in a subject comprising administering to the subject: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, and the enhancer compound or a pharmaceutically acceptable derivative thereof, are complementary PBP binding agents.

In some embodiments, there is provided a pharmaceutical composition comprising: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, and the enhancer compound or a pharmaceutically acceptable derivative thereof, are present in the concentrations lower than the corresponding minimum inhibitory concentrations.

In some embodiments, there is provided a method of treating a bacterial infection in a subject comprising administering to the subject: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, and the enhancer compound or a pharmaceutically acceptable derivative thereof, are present in the concentrations lower than the corresponding minimum inhibitory concentrations.

In some embodiments, there is provided a pharmaceutical composition comprising: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, and the enhancer compound or a pharmaceutically acceptable derivative thereof, are present in the concentrations equal to or higher than the corresponding minimum inhibitory concentrations.

In some embodiments, there is provided a method of treating a bacterial infection in a subject comprising administering to the subject: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, and the enhancer compound or a pharmaceutically acceptable derivative thereof, are present in the concentrations equal to or higher than the corresponding minimum inhibitory concentrations.

In some embodiments, there is provided a pharmaceutical composition comprising: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, is present at its minimum filamentation concentration and the enhancer compound or a pharmaceutically acceptable derivative thereof, is present at its minimum spheroplasting concentration.

In some embodiments, there is provided a method of treating a bacterial infection in a subject comprising administering to the subject: (a) at least one antibacterial agent or a pharmaceutically acceptable derivative thereof, and (b) an enhancer compound or a pharmaceutically acceptable derivative thereof; wherein the antibacterial agent or a pharmaceutically acceptable derivative thereof, is present at its minimum filamentation concentration and the enhancer compound or a pharmaceutically acceptable derivative thereof, is present at its minimum spheroplasting concentration.

The pharmaceutical compositions according to the invention may include one or more pharmaceutically acceptable carriers or excipients or the like, Typical, non-limiting examples of such carriers or excipient include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) ore are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compositions and methods according to the invention are also effective in preventing or treating bacterial infections that are caused by bacteria producing one or more beta-lactamase enzymes. The ability of compositions and methods according to the present invention to treat such resistant bacteria with typical beta-lactam antibiotics represents a significant improvement in the art.

In general, the use of an enhancer compound according to the invention results in increase in the antibacterial effectiveness of an antibacterial agent in a subject. The antibacterial effectiveness of one or more antibacterial agents may be increased, for example, by co-administering said antibacterial agent or a pharmaceutically acceptable derivative thereof with an enhancer compound or a pharmaceutically acceptable derivative thereof.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

Example 1

The use of trans-(2S,5R)-sulfuric acid mono-[2-(N'—[(R)-piperidin-3-carbonyl]-hydrazino carbonyl)-7-oxo-1,6-diaza-bicyclo[3.2.1]oct-6-yl] ester [compound of Formula (III)] as an Enhancer Compound

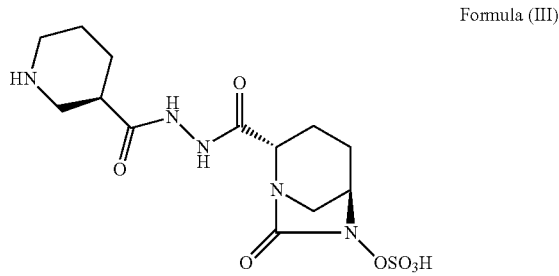

Formula (III)

A compound of Formula (III) was prepared using the procedure disclosed in PCT International Application No. PCT/IB2012/054290 and was evaluated for its PBP binding affinity profile. In a typical PBP binding assay for evaluating PBP binding affinity, 20 μl (final volume) of PBPs containing solution was incubated (30 min, 37° C.) in the presence of growing concentrations of compound of Formula (III), Cefepime and Mecillinam (range of concentrations tested 0.0156-2 mg/L) and afterwards labeled with a 25 μM concentration of the fluorescent penicillin Bocillin FL. The reaction mixtures were then denatured with 20 μl each of SDS-denaturing solution at 100° C. for 3 min PBPs were separated through 10% SDS polyacrylamide gel electrophoresis (Bio-Rad Laboratories, Hercules, Calif.). The protein gels were rinsed in water immediately after electrophoresis. Labeled PBPs were visualized using a BioRad Molecular Imager FX Pro (Bio-Rad Laboratories, Hercules, Calif.) (excitation at 488 nm and emission at 530 nm) and $IC_{50}$ values of compound of Formula (III), Cefepime and Mecillinam for the different PBPs were determined from triplicate independent experiments using the Quantity One software (Bio-Rad Laboratories, Hercules, Calif.) and compared using the Student's test. P values<0.05 were considered statistically significant. The results of these studies are given in Table 1.

The data in Table 1 shows that Cefepime binds to multiple PBPs with high affinity (except PBP 5/6). Mecillinam and the compound of Formula (III) bind selectively to *Pseudomonas* PBP2 with high affinity ($IC_{50}$ value of 1 μg/ml or less). Thus, Mecillinam and compound of Formula (III) can be said to be a "selective and high affinity PBP binder".

TABLE 1

$IC_{50}$ values of various compounds for different *Pseudomonas* PBPs

| | | $IC_{50}$ (μg/ml) | | |
|---|---|---|---|---|
| Sr. | *Pseudomonas* PBP | Cefepime | Mecillinam | Compound of Formula (III) |
| 1. | 1A | 0.12 ± 0.01 | >4 | >4 |
| 2. | 1B | 0.82 ± 0.07 | >4 | >4 |
| 3. | 2 | 2.71 ± 0.92 | 0.19 ± 0.02 | 0.26 ± 0.06 |

TABLE 1-continued

IC$_{50}$ values of various compounds for different *Pseudomonas* PBPs

| | | IC$_{50}$ (µg/ml) | | |
|---|---|---|---|---|
| Sr. | *Pseudomonas* PBP | Cefepime | Mecillinam | Compound of Formula (III) |
| 4. | 3 | 0.15 ± 0.07 | >4 | >4 |
| 5. | 4 | 2.52 ± 0.27 | >4 | >4 |
| 6. | 5/6 | >4 | >4 | >4 |

Next, the beta-lactamase stability of some of these compounds was evaluated. In a typical stability study, ESBL enzymes from *K. pneumoniae* S48 producing Metalo beta-lactamase (NDM4) and Class A (CTX-M, SHV, TEM) beta-lactamase were isolated from freshly grown culture by 5 repetitive cycles of freeze and thaw in liquid nitrogen. 80 µg/ml concentrations of Imipenem, Mecillinam and compound of Formula (III) were made in 0.5 ml of crude enzyme extract and incubated at 37° C. for 0, 1, 2 and 24 hours for enzymatic reaction to occur. After the stipulated incubation duration, the test compounds were extracted from the reaction mixture by the addition of 0.5 ml of Acetonitrile in 1:1 ratio (final concentration of test compound—40 µg/ml) and centrifuged at 12000 rpm for 2 min to separate precipitated protein. The activity of test compounds was measured from the supernatant by performing microbiological drug diffusion assay. For drug diffusion assay, Muller-Hinton Agar (MHA) seeded with *E. coli* ATCC 25922 was poured on to a bioassay plate placed on a flat surface and allowed to solidify. Appropriate concentration of the standalone and enzyme treated test compound dilutions were added to 6 mm wells cut with the help of a borer. The antibacterial activity of the test compounds was measured in terms of zones of inhibition appearing after 18-24 hours of incubation at 37° C. Measurement of diameter of zone of inhibition was undertaken to the nearest whole value with the help of ruler. The results of these stability studies are given in Tables 2a and 2b.

TABLE 2a

Antibacterial activity of various compounds against *E. coli* ATCC 25922 in absence of beta-lactamase enzymes

| | | Inhibition zone diameter (mm) | | | |
|---|---|---|---|---|---|
| Sr. | Compound (40 µg/ml) | 0 hour | 1 hour | 2 hours | 24 hours |
| 1. | Compound of Formula (III) | 16 | 16 | 16 | 16 |
| 2. | Mecillinam | 15.5 | 15.5 | 15.5 | 15.5 |
| 3. | Imipenem | 22 | 22 | 22 | 22 |

TABLE 2b

Stability of various compounds in presence of beta-lactamase enzymes

| | | Inhibition zone diameter (mm) after treatment with beta-lactamase enzyme | | | |
|---|---|---|---|---|---|
| Sr. | Compound (40 µg/ml) | 0 hour | 1 hour | 2 hours | 24 hours |
| 1. | Compound of Formula (III) | 16 | 16 | 16 | 16 |
| 2. | Mecillinam | 15.5 | 12 | 0 | 0 |
| 3. | Imipenem | 22 | 14 | 0 | 0 |

In these stability studies, the antibacterial activity (expressed in terms of inhibition zone diameters (mm)) of standalone test compounds (i.e. without any beta-lactamase treatment) was found to remain unaltered at 0, 1, 2 and 24 hours (Table 2a). The Table 2b shows the stability of various compounds in presence of beta-lactamase enzymes. The values of inhibition zone diameter (expressed in mm) for the compound of Formula (III), Mecillinam and Imipenem was 16, 15.5 and 22, respectively. The particular beta-lactamase used in this study is carbapenem hydrolyzing metallo beta-lactamase. As can be seen from the data in Table 2b, the compound of Formula (III) retained its antibacterial activity (as shown by unaltered inhibition zone diameter) even after incubating with the beta-lactamase for 24 hours, confirming that it was stable and not inactivated by the beta-lactamase. On the other hand, Imipenem and Mecillinam activity was highly compromised after treatment with the beta-lactamase indicating these were not stable to the beta-lactamase. The data in Table 1 and 2 confirm that the compound of Formula (III) is beta-lactamase stable and is also a selective and high affinity PBP binder. Thus, the compound of Formula (III) can be used as an enhancer compound according to the invention.

Example 2

Antibacterial Effectiveness of an Antibacterial Agent in Presence of an Enhancer Compound The antibacterial effectiveness of various antibacterial agents in presence of a compound of Formula (III) was investigated and the results are detailed below. In a typical study, overnight cultures in Trypticase soya broth (TSB) were brought to log phase by 1 in 10 dilution in fresh cation adjusted Mueller Hinton Broth (MHB) and incubation for 2.5 hours at 35° C. in orbital shaker. Log phase cultures were diluted to desired inoculums in flasks with MHB, containing various drug concentrations. Flasks were incubated at 35° C. in orbital shaker with rotational speed of 125 rpm. Viability count was determined by 1 in 10 serial dilutions of samples in normal saline and surface spreading of 10 µl of dilutions in duplicate on Trypticase soya agar plates. Plates were incubated for 24 hours at 35° C. and colonies were enumerated to determine the colony forming units (CFU) per ml volume. The results of these studies are described below.

Data describing efficacy of various antibacterial agents in presence of a compound of Formula (III) against *E. coli* ATCC 25922 strain is given in Tables 3 to 5. Table 3 details data obtained using Aztreonam, Table 4 using Cefoxitin and Table 5 using Cefsulodin. As can be seen, each of these compounds exhibited surprisingly and unexpectedly higher bactericidal action in presence of a compound of Formula (III) in comparison when these were used alone. It is also noteworthy that Aztreonam is known to be a sole PBP3 binder, Cefoxitin is a PBP5/6 binder and Cefsulodin is a PBP1a/b binder, which means that each of these compounds were binding to a PBP other than the one bound by the compound of Formula (III), which binds to PBP2. This suggests that the synergistic bactericidal effect may be obtained when the antibacterial agent and the enhancer compound exhibit complementary PBP binding profiles.

Table 3 details data on synergistic bactericidal action of Aztreonam in presence of a compound of Formula (III) in *E. coli* ATCC 25922. As can be seen, both Aztreonam and the compound of Formula (III) did not exhibit any bactericidal action when used standalone. Surprisingly, a combination of Aztreonam and the compound of Formula (III) exhibited synergistic bactericidal action.

TABLE 3

Synergistic bactericidal action of Aztreonam in presence of a compound of Formula (III) in *E. coli* ATCC 25922

| | | Bacterial count expressed in log (CFU/ml) | | | | |
|---|---|---|---|---|---|---|
| Sr. | Compound | 0 (hour) | 2 (hours) | 4 (hours) | 6 (hours) | 24 (hours) |
| 1. | Control | 7.47 | 8.0 | 8.88 | 8.95 | 9.18 |
| 2. | Aztreonam (1 µg/ml) | 7.47 | 7.48 | 7.47 | 7.48 | 7.5 |
| 3. | Compound of Formula (III) (2 µg/ml) | 7.47 | 7.85 | 7.88 | 8.26 | 8.34 |
| 4. | Aztreonam (1 µg/ml) + Compound of Formula (III) (2 µg/ml) | 7.47 | 5.98 | 5.52 | 5.08 | 3.0 |

Table 4 details data on synergistic bactericidal action of Cefoxitin in presence of a compound of Formula (III) in *E. coli* ATCC 25922. As can be seen, both Cefoxitin and the compound of Formula (III) did not exhibit any significant bactericidal action when used standalone. Surprisingly, a combination of Cefoxitin and the compound of Formula (III) exhibited synergistic bactericidal action.

Table 5 details data on synergistic bactericidal action of Cefsulodin in presence of a compound of Formula (III) in *E. coli* ATCC 25922. As can be seen, both Cefsulodin and the compound of Formula (III) did not exhibit any bactericidal action when used standalone. Surprisingly, a combination of Cefsulodin and the compound of Formula (III) exhibited synergistic bactericidal action.

TABLE 4

Synergistic bactericidal action of Cefoxitin in presence of a compound of Formula (III) in *E. coli* ATCC 25922

| | | Bacterial count expressed in log (CFU/ml) | | | | |
|---|---|---|---|---|---|---|
| Sr. | Compound | 0 (hour) | 2 (hours) | 4 (hours) | 6 (hours) | 24 (hours) |
| 1. | Control | 7.47 | 8.0 | 8.88 | 8.95 | 9.18 |
| 2. | Cefoxitin (1 µg/ml) | 7.47 | 7.11 | 6.7 | 6.54 | 9 |
| 3. | Compound of Formula (III) (2 µg/ml) | 7.47 | 7.85 | 7.88 | 8.26 | 8.34 |
| 4. | Cefoxitin (1 µg/ml) + compound of Formula (III) (2 µg/ml) | 7.47 | 5.2 | 3.93 | 3.0 | 1.0 |

TABLE 5

Synergistic bactericidal action of Cefsulodin in presence of a compound of Formula (III) in *E. coli* ATCC 25922

| | | Bacterial count expressed in log (CFU/ml) | | | | |
|---|---|---|---|---|---|---|
| Sr. | Compound | 0 (hour) | 2 (hours) | 4 (hours) | 6 (hours) | 24 (hours) |
| 1. | Control | 7.47 | 8.0 | 8.88 | 8.95 | 9.18 |
| 2. | Cefsulodin (16 µg/ml) | 7.47 | 8.4 | 8.8 | 8.3 | 9 |
| 3. | Compound of Formula (III) (2 µg/ml) | 7.47 | 7.85 | 7.88 | 8.26 | 8.34 |
| 4. | Cefsulodin (16 µg/ml) + compound of Formula (III) (2 µg/ml) | 7.47 | 4.85 | 4.08 | 3.2 | 2.0 |

Tables 6 and 7 detail data on synergistic bactericidal action of Aztreonam (sole PBP3 binding agent) and Cefsulodin (PBP3 binding agent) against *P. aeruginosa* PAO1 strain confirming the synergistic action obtained due to complementary PBP binding profiles of the antibacterial agent and the enhancer compound.

Table 6 details data on synergistic bactericidal action of Aztreonam in presence of a compound of Formula (III) in *P. aeruginosa* PAO1 strain. As can be seen, both Aztreonam and the compound of Formula (III) did not exhibit any bactericidal action when used standalone. Surprisingly, a combination of Aztreonam and the compound of Formula (III) exhibited synergistic bactericidal action.

Table 7 details data on synergistic bactericidal action of Cefsulodin in presence of a compound of Formula (III) in *P. aeruginosa* PAO1 strain. As can be seen, compound of Formula (III) did not exhibit any bactericidal action when used standalone. Even stand alone Cefsulodin failed to cause consistent killing till 24 hour. Surprisingly, a combination of Cefsulodin and the compound of Formula (III) exhibited synergistic bactericidal action consistently till 24 hours.

TABLE 6

Synergistic bactericidal action of Aztreonam in presence of a compound of Formula (III) in *P. aeruginosa* PAO1

| | | Bacterial count expressed in log (CFU/ml) | | | | |
|---|---|---|---|---|---|---|
| Sr. | Compound | 0 (hour) | 2 (hours) | 4 (hours) | 6 (hours) | 24 (hours) |
| 1. | Control | 5.74 | 6.74 | 7.78 | 8.16 | 8.78 |
| 2. | Aztreonam (2 µg/ml) | 5.74 | 6.3 | 6.65 | 6.54 | 7.15 |
| 3. | Compound of Formula (III) (4 µg/ml) | 5.74 | 6.5 | 7.6 | 7.9 | 8.8 |
| 4. | Aztreonam (2 µg/ml) + compound of Formula (III) (4 µg/ml) | 5.74 | 5.54 | 4.02 | 3.54 | 2.2 |

TABLE 7

Synergistic bactericidal action of Cefsulodin in presence of a compound of Formula (III) in *P. aeruginosa* PAO1

| | | Bacterial count expressed in log (CFU/ml) | | | | |
|---|---|---|---|---|---|---|
| Sr. | Compound | 0 (hour) | 2 (hours) | 4 (hours) | 6 (hours) | 24 (hours) |
| 1. | Control | 6.81 | 7.7 | 8.0 | 8.53 | 8.78 |
| 2. | Cefsulodin (2 μg/ml) | 6.81 | 6.48 | 5.07 | 4.74 | 9 |
| 3. | Compound of Formula (III) (4 μg/ml) | 6.81 | 7.23 | 7.18 | 7.5 | 8.2 |
| 4. | Cefsulodin (2 μg/ml) + compound of Formula (III) (4 μg/ml) | 6.81 | 5.27 | 4.24 | 3.54 | 2 |

Tables 8 and 9 detail data on synergistic bactericidal action of Cefepime in presence of a compound of Formula (III) against highly resistant strains of *K. pneumoniae* and *A. baumannii*, which produce metallo beta-lactamases (MBL) and carbapenem hydrolyzing class D beta-lactamases (CHDL) for example OXA enzymes. Lack of bactericidal action of Imipenem and Cefepime in these cases suggests expression of metallo beta-lactamases (MBL) and carbapenem hydrolyzing class D beta-lactamases (CHDL) enzymes by the strains respectively.

For *K. pneumoniae* S48, clinically used ESBL inhibitor such as Clavulanic acid that do not inhibit MBLs was ineffective in causing bacterial killing in combination with Cefepime. Similarly inconsistent cidal response was observed for a combination of Mecillinam and Cefepime despite a complementary PBP2 & PBP3/1a/1b binding due to the enzymatic inactivation of Mecillinam and Cefepime both. Inconsistent cidal response was also observed with Imipenem due to its enzymatic inactivation. It was only with the combination of beta-lactamase stable PBP2 binder such as the compound of Formula (III) that Cefepime evoked a consistently powerful bactericidal action. The experiment clearly demonstrates the role of beta-lactamase stable PBP2 binder (i e enhancer compound) in enabling overcome metallo beta-lactamase (MBL) mediated resistance.

TABLE 8

Synergistic bactericidal action of Cefepime in presence of a compound of Formula (III) against *K. pneumonia* S48 expressing multiple ESBLs including carbapenem hydrolyzing metallo beta-lactamase (MBL) [ESBL Resistance: MBL (NDM4) and Class A (CTX-M, SHV, TEM)]

| | | Bacterial count expressed in log (CFU/ml) | | | | |
|---|---|---|---|---|---|---|
| Sr. | Compound | 0 (hour) | 2 (hours) | 4 (hours) | 6 (hours) | 24 (hours) |
| 1. | Control | 5.5 | 6.3 | 7.74 | 8.0 | 8.54 |
| 2. | Cefepime (8 μg/ml) | 5.5 | 5.04 | 5.88 | 6.93 | 8.54 |
| 3. | Compound of Formula (III) (2 μg/ml) | 5.5 | 5.4 | 3.5 | 3.6 | 8.34 |
| 4. | Cefepime (8 μg/ml) + compound of Formula (III) (2 μg/ml) | 5.5 | 3.0 | 2.15 | 2.15 | 1.85 |
| 5. | Cefepime (8 μg/ml) + Clavulanic acid (2 μg/ml) | 5.5 | 5.2 | 6.2 | 7.2 | 8.3 |
| 6. | Cefepime (8 μg/ml) + Mecillinam (2 μg/ml) | 5.5 | 3.0 | 4.17 | 5.74 | 9.0 |
| 7. | Imipenem (8 μg/ml) | 5.5 | 3.0 | 3.0 | 4.0 | 8.69 |

In case of *A. baumannii*, producing carbapenem hydrolyzing Class D lactamases (CHDL) producing OXA enzymes (Table 9) it was only the combination of compound of Formula (III) and Cefepime that generated significant bactericidal action as compared to individual agents highlighting the key role of beta-lactamase PBP2 binder in overcoming carbapenem hydrolyzing Class D OXA mediated resistance.

TABLE 9

Synergistic bactericidal action of Cefepime in presence of a compound of Formula (III) against *Acinetobacter baumannii* NCTC 13304 producing carbapenem hydrolyzing Class D OXA enzyme (OXA 27)

| | | Bacterial count expressed in log (CFU/ml) | | | | |
|---|---|---|---|---|---|---|
| Sr. | Compound | 0 (hour) | 2 (hours) | 4 (hours) | 6 (hours) | 8 (hours) |
| 1. | Control | 6.3 | 7.6 | 8.1 | 8.2 | 8.2 |
| 2. | Cefepime (8 μg/ml) | 6.3 | 7.3 | 7.5 | 7.8 | 8.0 |
| 3. | Compound of Formula (III) (8 μg/ml) | 6.3 | 7.5 | 7.9 | 8.1 | 8.1 |
| 4. | Cefepime (8 μg/ml) + compound of Formula (III) (8 μg/ml) | 6.3 | 6.2 | 4 | 3.5 | 3.5 |
| 5. | Imipenem (16 μg/ml) | 6.3 | 7.2 | 7.9 | 7.9 | 8 |

Table 10 details data on bactericidal action of Cefepime in presence of a compound of Formula (III) against *Pseudomonas aeruginosa* NCTC 13437 strain producing carbapenem hydrolyzing MBL (VIM 10) & Class A (VEB1) enzymes.

TABLE 10

Synergistic bactericidal action of Cefepime in presence of a compound of Formula (III) against *Pseudomonas aeruginosa* NCTC 13437 strain producing carbapenem hydrolyzing MBL (VIM 10) & Class A (VEB1)

| | | Bacterial count expressed in log (CFU/ml) | | | | |
|---|---|---|---|---|---|---|
| Sr. | Compound | 0 (hour) | 2 (hours) | 4 (hours) | 6 (hours) | 12 (hours) |
| 1. | Control | 6.0 | 6.65 | 7.34 | 7.88 | 9.0 |
| 2. | Cefepime | 6.0 | 6.49 | 7.74 | 8.02 | 8.8 |

TABLE 10-continued

Synergistic bactericidal action of Cefepime in presence of a compound of Formula (III) against *Pseudomonas aeruginosa* NCTC 13437 strain producing carbapenem hydrolyzing MBL (VIM 10) & Class A (VEB1)

| | | Bacterial count expressed in log (CFU/ml) | | | | |
|---|---|---|---|---|---|---|
| Sr. | Compound | 0 (hour) | 2 (hours) | 4 (hours) | 6 (hours) | 12 (hours) |
| | (8 µg/ml) | | | | | |
| 3. | Compound of Formula (III) (8 µg/ml) | 6.0 | 6.55 | 5.9 | 5.81 | 6.2 |
| 4. | Cefepime (8 µg/ml) + compound of Formula (III) (8 µg/ml) | 6.0 | 5.74 | 5.5 | 3.78 | 3.44 |
| 5. | Imipenem (16 µg/ml) | 6.0 | 7.2 | 7.9 | 7.9 | 8.3 |

Table 11 details data on synergistic antibacterial action of Meropenm in presence of a compound of Formula (III) and in overcoming outer membrane porins (OMP) mediated resistance in *K. pneumoniae* clinical isolates. Higher Meropenem MIC values indicate the role of OMP mediated resistance adversely impacting the uptake of Meropenem. Surprisingly, a remarkable reduction in the MIC of Meropenem was observed in presence of a compound of Formula (III) demonstrating that an enzymatically stable PBP2 binding agent helps Meropenam overcome OMP mediated resistance. In a typical procedure for determining MIC values, overnight grown bacterial cultures were diluted appropriately and inoculated on the agar media containing doubling concentrations of the test compounds. Observation for growth or no growth was performed after 16-20 hours of incubation at 35±2° C. in ambient air. The overall procedure was performed as per Clinical and Laboratory Standards Institute (CLSI) recommendations (Clinical and Laboratory Standards Institute (CLSI), Performance Standards for Antimicrobial Susceptibility Testing, 20th Informational Supplement, M 100-S20, Volume 30, No. 1, 2010).

TABLE 11

Synergistic antibacterial activity of Meropenem in presence of a compound of Formula (III) in organisms exhibiting OMP mediated resistance.

| | | | MIC expressed in µg/ml | | |
|---|---|---|---|---|---|
| Sr. | Organism | Mechanism of Resistance | Meropenem | Compound of Formula (III) | Meropenem + a compound of Formula (III) (8 µg/ml |
| 1. | *K. pneumoniae* J 101 | TEM1, SHV12, OMP | 4 | >32 | 0.25 |
| 2. | *K. pneumoniae* J 102 | TEM1, SHV5, OMP | 8 | >32 | 0.25 |
| 3. | *K. pneumoniae* J 104 | TEM1, SHV11, CTX-M, OMP | 4 | >32 | 0.12 |
| 4. | *K. pneumoniae* J 105 | TEM1, SHV2, CTX-M, OMP | 4 | >32 | 0.25 |

The data provided in the above examples indicate that a combination comprising at least one antibacterial agent or a pharmaceutically acceptable derivative thereof, and an enhancer compound or a pharmaceutically acceptable derivative thereof; wherein the enhancer compound is: (i) beta-lactamase stable, and (ii) a selective and high affinity PBP binder; can be effectively used in treating or controlling bacterial infections (even those being caused by bacteria that have developed various mechanisms of resistance) in a subject. The data presented herein also indicates that antibacterial effectiveness of an antibacterial agent in a subject can be increased by co-administering said antibacterial agent or a pharmaceutically acceptable derivative thereof with an enhancer compound or a pharmaceutically acceptable derivative thereof; wherein the enhancer compound is: (i) beta-lactamase stable, and (ii) a selective and high affinity PBP binder.

Example 3

Synergistic Killing Effect of Combination of an Antibacterial Agent and an Enhancer Compound The synergistic killing effect of the combinations according to invention was studied by performing time kill studies. In a typical time kill study, the freshly grown cultures were diluted to the required cell density (initial starting inoculum) in Cation adjusted Muller Hinton broth medium (BD, USA). The antibacterial agents (either alone or in combination) at the required concentrations were added into the culture-containing medium. The samples were incubated under shaking condition (120 rpm) at 37° C. Enumeration of viable bacterial count was done every 2 hour by diluting in normal saline and plating on to the Tryptic Soya Agar plates (BD, USA). The plates were incubated for 24 hours to arrive at the viable bacterial count. The results are expressed in terms of Log CFU per ml. In general, the decrease of 1 Log CFU/ml, corresponds to 90% killing of bacteria. Similarly, 2 Log CFU/ml reductions indicates to 99% killing of bacteria and 3 Log CFU/ml reductions is equal to 99.9% killing of bacteria.

It was surprisingly found that combining complementary binding agents at their respective MFC (concentration at which about 80% of bacterial cells elongate) and MSC (concentration at which about 80% of bacterial cells convert in to spheroplast) generate potent cidal action against even highly resistant bacterial strains. Cefepime exhibited high affinity towards PBP3 and it was observed that the sub-MIC concentration of Cefepime was enough to convert the normal bacterial cells to filaments. Similarly, compound of Formula (III), an enhancer, exhibited higher affinity towards PBP2 and at its sub-MIC concentration converted the normal bacterial cells to spheroplasts. In other words combination of Cefepime at its MFC concentration and compound of Formula (III) at its MSC concentration exhibited potent antibacterial activity. Therefore rather than MIC, the parameters of MFC and MSC concentrations driving the cidal synergy exemplifies the critical importance of these parameters in unleashing the bactericidal action of combinations operating through the enhancer mechanism of complementary PBP binding.

The Table 12 reveals the minimum inhibitory concentration (MIC), minimum filamentation concentration (MFC) and minimum spheroplasting concentration (MSC) for Cefepime and compound of Formula (III) against *K. pneumonia* B88 and *P. mirabilis* G 186. As can be seen from the data, the higher MIC values obtained for both Cefepime and Compound of Formula (III) represents higher resistance against *K. pneumoniae* and *P. mirabilis*. However, the MFC values for Cefepime and MSC values for compound of Formula (III), an enhancer compound, were found to be significantly lower than the corresponding MIC values.

The synergistic cidal activity of Cefepime and combination of compound of Formula (III) at their respective MFC and MSC was studied against multi drug resistant (MDR) *Klebsiella pneumoniae* B 88 and *P. mirabilis* G 186. The results are shown in Table 13 and Table 14. *Klebsiella pneumoniae* B 88 produces NDM, SHV and TEM beta-lactamases, and *P. mirabilis* G 186. As can be seen from the Table 13, both Cefepime and compound of Formula (III) (an enhancer compound), at their corresponding MFC and MSC concentration did not exhibit antibacterial activity against *Klebsiella pneumoniae* B 88. However, surprisingly, it has been found that the combination of Cefepime and compound of Formula (III) (an enhancer compound), at their corresponding MFC and MSC concentration exhibited potent antibacterial activity against multidrug resistant (MDR) *Klebsiella pneumoniae* B 88. Similarly, it can be seen from the Table 14, that both Cefepime and compound of Formula (III) (an enhancer compound), at their corresponding MFC and MSC concentration did not exhibit antibacterial activity against *P. mirabilis* G 186. However, surprisingly it has been found that the combination of Cefepime and compound of Formula (III) (an enhancer compound), and Cefepime at their corresponding MFC and MSC concentration exhibited potent antibacterial activity against multidrug resistant (MDR) *P. mirabilis* G 186.

The compound of Formula (III) acts as an enhancer with features such as high affinity PBP2 binding and stability to beta-lactamases. These features help attain high degree of cidal synergy in combination with a beta-lactamases labile complementary PBP binding agent even against highly resistant metallo beta-lactamase producing strains.

TABLE 12

MIC, MSC and MFC concentrations for Cefepime and compound of Formula (III) against *K. pneumonia* B88 and *P. mirabilis* G 186.

| | | Cefepime | | Compound of Formula (III) | |
|---|---|---|---|---|---|
| Organism | Beta-lactamases | MIC (μg/ml) | MFC (μg/ml) | MIC (μg/ml) | MSC (μg/ml) |
| *K. pneumoniae* B88 | NDM, SHV, TEM | >64 | 8 | 8 | 0.12 |
| *P. mirabilis* G 186 | NDM, TEM | >64 | 8 | >64 | 0.25 |

TABLE 13

Synergistic Cidal activity of compound of Formula (III) when combined with Cefepime at their respective MSC & MFC concentrations for MDR *Klebsiella pneumoniae* B 88 producing NDM, SHV & TEM beta-lactamases.

| | | Bacterial count ($Log_{10}$ CFU/ml) | | | | |
|---|---|---|---|---|---|---|
| Sr. | Combination | 0 hour | 2 hours | 4 hours | 6 hours | 8 hours |
| 1. | Control (No active ingredient) | 6.14 | 7.39 | 8.47 | 8.90 | 9.2 |
| 2. | Cefepime (8 mcg/ml) MFC Concentration | 6.14 | 6.65 | 8.30 | 9.11 | 9.04 |
| 3. | Compound of Formula (III) (0.12 mcg/ml) MSC Concentration | 6.14 | 7.3 | 7.8 | 7.9 | 8.5 |
| 4. | Cefepime (8 mcg/ml) + Compound of Formula (III) (0.12 mcg/ml) | 6.14 | 4.54 | 3.86 | 4 | 4.6 |
| 5 | Imepenem (8 mcg/ml) | 6.14 | 8.65 | 8.7 | 8.74 | 8.78 |

TABLE 14

Synergistic Cidal activity of compound of Formula (III) when combined with Cefepime at their respective MSC & MFC concentrations for MDR *P. mirabilis* G 186 producing NDM & TEM β-lactamases.

| | | Bacterial count ($Log_{10}$ CFU/ml) | | | | |
|---|---|---|---|---|---|---|
| Sr. | Combination | 0 hour | 2 hours | 4 hours | 6 hours | 8 hours |
| 1. | Control (No active ingredient) | 6.58 | 7.57 | 8.26 | 9.02 | 9.24 |
| 2. | Cefepime (8 mcg/ml) (MFC concentration) | 6.58 | 6.04 | 7.93 | 8.66 | 8.85 |
| 3. | Compound of Formula (III) (0.25 mcg/ml) (MSC concentration) | 6.58 | 7.2 | 7.7 | 8.43 | 8.6 |
| 4. | Cefepime (8 mcg/ml) + Compound of Formula (III) (0.25 mcg/ml) | 6.58 | 6.2 | 4.65 | 4.3 | 3.48 |
| 5 | Imepenem (8 mcg/ml) | 6.58 | 7.2 | 9.45 | 8.65 | 8.85 |

Thus, the Tables 12-14 show the potent antibacterial activity of the combination according to invention at their corresponding sub-minimum inhibitory concentrations (sub-MICs). The combination of compound of Formula (III) (an enhancer) and Cefepime at their corresponding MSC and MFC values, which are much lower than their corresponding MIC values, exhibited potent antibacterial activity against multi drug resistant (MDR) bacterial strains. Thus combination of an antibacterial agent and an enhancer compound has tremendous beneficial effect in inhibiting highly resistant bacterial strains demonstrating the noteworthy therapeutic advance in the treatment of infections caused by such pathogens.

The invention claimed is:

1. A method of treating a bacterial infection, comprising administering to a subject in need thereof effective amount of: (a) at least one antibacterial agent or pharmaceutically acceptable derivative thereof, and (b) an enhancer compound or a pharmaceutically acceptable derivative thereof, wherein the enhancer compound is trans-(2S,5R)-sulfuric acid mono-[2-(N'—[(R)-piperidin-3-carbonyl]-hydrazino carbonyl)-7-oxo-1,6-diaza-bicyclo[3.2.1]oct-6-yl] ester.

2. A method of increasing antibacterial effectiveness of an antibacterial agent or a pharmaceutically acceptable salt thereof, comprising co-administering to a subject in need thereof said antibacterial agent or pharmaceutically acceptable derivative thereof with an enhancer compound or a pharmaceutically acceptable derivative thereof, wherein the enhancer compound is trans-(2S,5R)-sulfuric acid mono-[2-(N'—[(R)-piperidin-3-carbonyl]-hydrazino carbonyl)-7-oxo-1,6-diaza-bicyclo[3.2.1]oct-6-yl] ester.

3. The method according to any one of claims 1 and 2, wherein the antibacterial agent is selected from the group consisting of aminoglycosides, ansamycins, carbacephems, penems, carbapenems, cephalosporins, cephamycins, lincosamides, lipopeptides, macrolides, monobactams, nitrofurans, penicillins, polypeptides, quinolones, sulfonamides, tetracyclines, and oxazolidinone antibacterial agents.

4. The method according to any one of claims 1 and 2, wherein the enhancer compound or pharmaceutically acceptable derivative thereof is present at an amount of from about 0.01 to about 10 grams per gram of the antibacterial agent or pharmaceutically acceptable derivative thereof.

5. The method according to any one of claims 1 and 2, wherein the enhancer compound or pharmaceutically acceptable derivative thereof is capable of selectively binding to one or more essential penicillin binding proteins (PBPs).

6. The method according to any one of claims 1 and 2, wherein the antibacterial agent or pharmaceutically acceptable derivative thereof, and the enhancer compound or pharmaceutically acceptable derivative thereof are complementary penicillin binding proteins (PBPs).

7. The method according to any one of claims 1 and 2, wherein the enhancer compound or pharmaceutically acceptable derivative thereof, and the antibacterial agent or pharmaceutically acceptable derivative thereof are present in concentrations lower than corresponding minimum inhibitory concentrations.

8. The method according to any one of claims 1 and 2, wherein the antibacterial agent or pharmaceutically acceptable derivative thereof is present at its minimum filamentation concentration and the enhancer compound or pharmaceutically acceptable derivative thereof is present at its minimum spheroplasting concentration.

9. The method according to any one of claims 1 and 2, wherein the pharmaceutically acceptable derivative is a pharmaceutically acceptable salt.

10. The method according to any one of claims 1 and 2, wherein the enhancer compound or pharmaceutically acceptable derivative thereof, and the antibacterial agent or pharmaceutically acceptable derivative thereof are present in concentrations equal to corresponding minimum inhibitory concentrations.

11. The method according to any one of claims 1 and 2, wherein the enhancer compound or pharmaceutically acceptable derivative thereof, and the antibacterial agent or pharmaceutically acceptable derivative thereof are present in concentrations higher than corresponding minimum inhibitory concentrations.

* * * * *